United States Patent [19]

Bright et al.

[11] Patent Number: 5,502,273
[45] Date of Patent: Mar. 26, 1996

[54] PRODUCTION OF POLYHYDROXY ALKANOATE IN PLANTS

[75] Inventors: Simon W. J. Bright, Marlow, Bucks; David Byrom, Cleveland; Philip A. Fentem, Berkshire, all of England

[73] Assignee: Zeneca Limited, London, United Kingdom

[21] Appl. No.: 314,439

[22] Filed: Sep. 28, 1994

Related U.S. Application Data

[63] Continuation of Ser. No. 181,370, Jan. 14, 1994, abandoned, which is a continuation of Ser. No. 873,429, Apr. 24, 1992, abandoned.

[30] Foreign Application Priority Data

Apr. 24, 1991 [GB] United Kingdom ............ 9108756

[51] Int. Cl.$^6$ .............................. A01H 5/00; C12N 5/14; C12N 15/00; C12N 15/52; C12P 7/62
[52] U.S. Cl. ................... 800/205; 800/DIG. 17; 435/172.3; 435/240.49; 435/135; 435/141; 435/142; 435/69.1
[58] Field of Search ................ 800/205; 435/69.1, 435/172.3, 240.2, 135, 141, 142; 935/35, 67

[56] References Cited

FOREIGN PATENT DOCUMENTS 9100917  1/1991  WIPO.

OTHER PUBLICATIONS

Janes et al (990) "Novel Biodegradable Microbial Polymers", A. E. Daves (Ed.) Kluwer Academic Rubl., Netherlands, pp. 175–190.
Moloney et al (1989) Plant Cell Reports 8:238–242.
R. Pool (1989) Science 245:1187–1189.
Qu et al (1990) J. Biol. Chem. 265 (4):2238–22–43.
Cashmore et al (1985) Bio/Technology 3:803–808.
Tierney et al (1987) Planta 172:356–363.

*Primary Examiner*—David T. Fox
*Assistant Examiner*—Elizabeth F. McElwain
*Attorney, Agent, or Firm*—Cushman Darby & Cushman

[57] ABSTRACT

A plant which produces polyhydroxyalkanoate polymer has a recombinant genome which contains one or more than one of the genes specifying enzymes critical to the polyhydroxyalkanoate biosynthetic pathway which occurs in certain micro-organisms such as *Alcaligenes eutrophus* which naturally produce same. The plant species is preferably an oil-producing plant.

6 Claims, 6 Drawing Sheets

FIG. 2A

- AvaI (2)
- SmaI (4)
- AccI (73)
- (176) DdeI
- PleI (527)
- BspMI (661)
- (751) AvaII
- (983) NotI
- AvaII (944)
- (1075) XmnI
- NcoI (1097)
- (1080) DdeI
- AvaII (1126)
- BspMI (1211)
- (1336) AvaI
- PleI (1368)
- (1424) BglII
- PstI (1610)
- (1602) AvaII
- BspMI (1613)
- (1621) SacI
- AccI (1928)
- (1927) SalI
- AccI (2066)
- (2065) SalI
- BspMI (2114)
- BspMI (2144)
- (2163) KpnI
- BspMI (2171)
- (2187) PstI
- BspMI (2180)
- (2200) KpnI
- SacI (2192)
- AvaII (2232)
- AvaII (2297)
- (2442) PleI
- AvaII (2495)
- BspMI (2652)
- StuI (2657)
- PstI (2663)
- BspMI (2826)
- AvaI (2964)
- (3115) SalI
- AccI (3116)
- (3130) SalI
- AccI (3131)
- AvaI (3438)
- AvaII (3614)
- AvaII (3630)
- StuI (3652)
- AvaII (3915)
- PleI (3950)
- DdeI (3958)
- PleI (4143)
- BspMI (4307)
- NcoI (4444)
- PleI (4643)
- BspMI (4703)
- XmnI (4826)
- DdeI (4898)
- PstI (4984)
- EcoRI (5196)

Restriction enzyme sites.

| Enzyme | Sites |
|---|---|
| AccI | 73, 1928, 2066, 3116, 3131 |
| AvaI | 2, 1336, 2964, 3438 |
| AvaII | 751, 944, 1126, 1602, 2232, 2297, 2495, 3614, 3630, 3915 |
| BamHI | – |
| BanII | – |
| BglII | 1424 |
| BspMI | 661, 1211, 1613, 2114, 2144, 2171, 2186, 2652, 2826, 4307, 4703 |
| DdeI | 176, 1080, 3958, 4898 |
| EcoRI | 5196 |
| HincII | – |
| HindIII | – |
| KpnI | 2163, 2200 |
| NcoI | 1097, 4444 |
| NotI | 983 |
| PleI | 527, 1368, 2442, 3950, 4143, 4643 |
| PstI | 1610, 2183, 2663, 4984 |
| Sau3AI | – |
| SacI(SstI) | 1621, 2192 |
| SalI | 1927, 2065, 3115, 3130 |
| SmaI | 4 |
| SphI | – |
| StuI | 2657, 3652 |
| XbaI | – |
| XmaI | – |
| XmnI | 1075, 4826 |

FIG. 2B

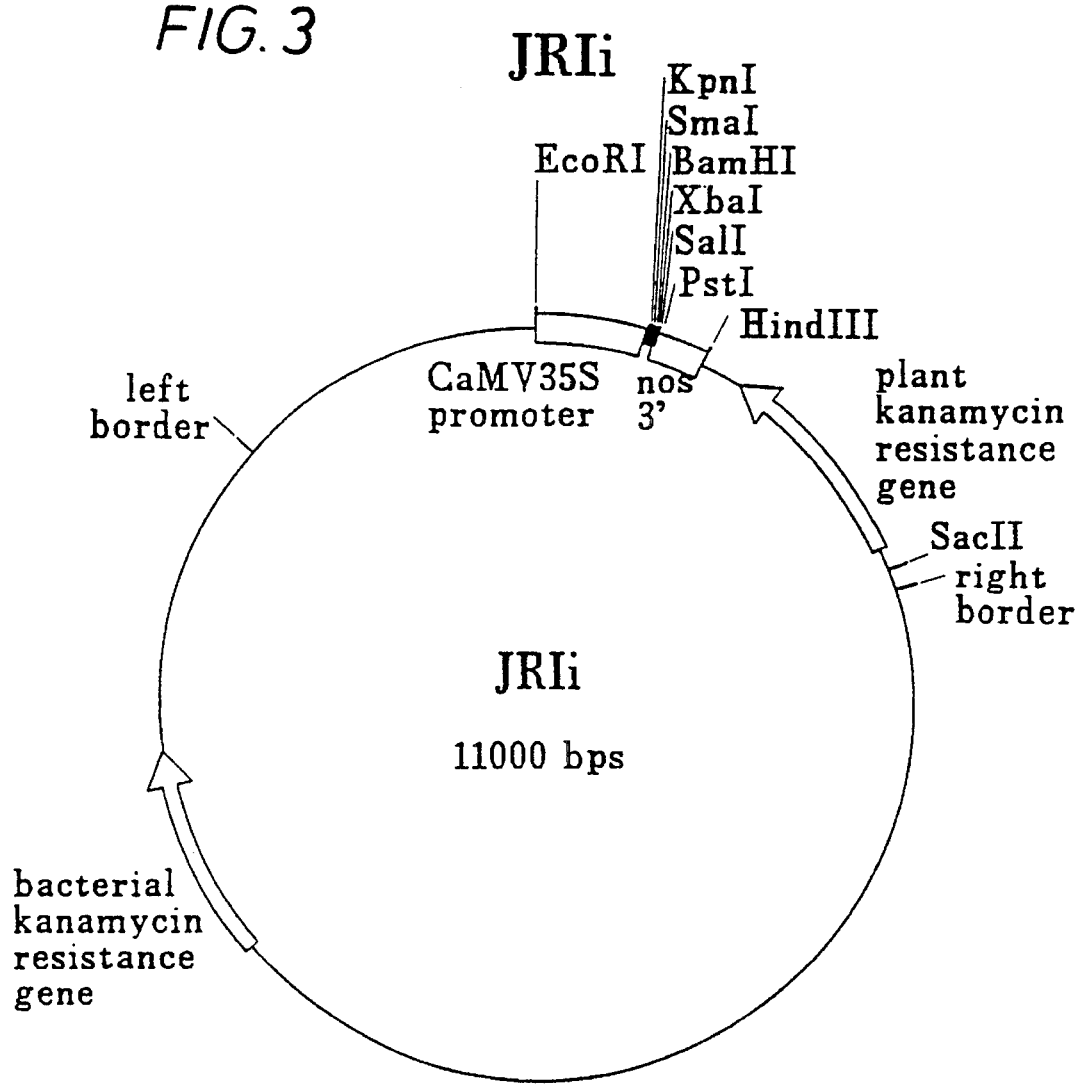
FIG. 3 The plant expression vector pJR1i

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

```
AAATGGCTTC TATGATATCC TCTTCAGCT                                    29
```

( 2 ) INFORMATION FOR SEQ ID NO:2:

( i ) SEQUENCE CHARACTERISTICS:
        ( A ) LENGTH: 47 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

```
ACGATGACAA CGTCAGTCAT GCACTTTACT CTTCCACCAT TGCTTGT                47
```

( 2 ) INFORMATION FOR SEQ ID NO:3:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

```
ATTACAAGCA ATGGTGGAAG AGTAAAGTGC ATGACTGACG TTGTCATCGT             50
```

( 2 ) INFORMATION FOR SEQ ID NO:4:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

```
ACCCCTTCCT TATTTGCGCT CGACT                                        25
```

( 2 ) INFORMATION FOR SEQ ID NO:5:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

```
ACCATCGATG GATGGCTTCT ATGATATCCT CTTCAGCT                                    38
```

( 2 ) INFORMATION FOR SEQ ID NO:6:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

```
ATGCGCTGAG TCATGCACTT TACTCTTCCA CCATTGCTTG TAAT                             44
```

PRODUCTION OF POLYHYDROXY ALKANOATE IN PLANTS

This is a continuation of application Ser. No. 08/181,370, filed on Jan. 14, 1994, which was abandoned upon the filing hereof, which is a Rule 62 continuation of application Ser. No. 07/873,429, filed Apr. 24, 1992, which is abandoned.

BACKGROUND OF THE INVENTION

This invention relates to the production of polyhydroxyalkanoate in plants.

Poly-3-hydroxybutyrate (PHB) is a linear polyester of D(−)-3-hydroxybutyrate. It was first discovered in *Bacillus megaterium* in 1925. Polyhydroxybutyrate accumulates in intracellular granules of a wide variety of bacteria. The granules appear to be membrane bound and can be stained with Sudan Black dye. The polymer is produced under conditions of nutrient limitation and acts as a reserve of carbon and energy. The molecular weight of the polyhydroxybutyrate varies from around 50,000 to greater than 1,000,000, depending on the micro-organisms involved, the conditions of growth, and the method employed for extraction of the polyhydroxybutyrate. Polyhydroxybutyrate is an ideal carbon reserve as it exists in the cell in a highly reduced state, (it is virtually insoluble), and exerts negligible osmotic pressure.

Polyhydroxybutyrate and related polyhydroxyalkanoates, such as poly-3-hydroxyvalerate and poly-3-hydroxyoctanoate, are biodegradable thermoplastics of considerable commercial importance.

The terms "polyhydroxyalkanoate" and "PHA" as used hereinafter include polymers of 3-hydroxybutyrate, polymers of related hydroxyalkanoates such as 3-hydroxyvalerate, 3-hydroxyhexanoate, 3-hydroxyoctanoate, 3-hydroxydecanoate, and also copolymers and mixtures of more than one of these hydroxyalkanoates.

Polyhydroxyalkanoate is biodegradable and is broken down rapidly by soil micro-organisms. It is thermoplastic (it melts at 180° C.) and can readily be moulded into diverse forms using technology well-established for the other thermoplastics materials such as high-density polyethylene which melts at around the same temperature (190° C.). The material is ideal for the production of biodegradable packaging which will degrade in landfill sites and sewage farms. The polymer is biocompatible, as well as biodegradable, and is well tolerated by the mammalian, including human, body; its degradation product, 3-hydroxybutyrate, is a normal mammalian metabolite. Polyhydroxybutyrate degrades only slowly in the body making it suitable for medical applications where long term degradation is required.

Polyhydroxyalkanoate, produced by the micro-organism *Alcaligenes eutrophus*, is manufactured, as a copolymer of polyhydroxybutyrate and polyhydroxyvalerate, by Imperial Chemical Industries PLC and sold under the Trade Mark BIOPOL. The nature of the polymer, for example the proportions of PHB and PHV is determined by the substrate supplied in the fermentation. It is normally supplied in the form of pellets for thermoprocessing. However, polyhydroxyalkanoate is more expensive to manufacture by existing methods than, say, polyethylene. It is, therefore, desirable that new, more economic production of polyhydroxyalkanoate be provided.

SUMMARY OF THE INVENTION

An object of the present invention is to provide materials and a method for the efficient production of polyhydroxyalkanoate.

According to the present invention there is provided a plant adapted for the production of polyhydroxyalkanoate comprising a recombinant genome of an oil-producing plant, which genome contains genes encoding enzymes necessary for catalysing the production of polyhydroxy-alkanoate together with gene regulatory sequences directing expression of the said genes to target plant cell components.

These regulatory sequences include promoter sequences directing expression of the biosynthetic pathway specifically to the developing seed, and transit peptide sequences targeting the enzymes to appropriate subcellular compartments.

The genes encoding the enzyme or enzymes necessary for the catalysis of polyhydroxyalkanoate production may be isolated from a micro-organism, such as *Alcaligenes eutrophus*, which is known to produce polyhydroxybutyrate and other polyhydroxyalkanoates.

It is preferable, for reasons which will later be explained, that the plant be of a species which produces substantial quantities of oil, rather than starch. Such plant species are well known and are simply referred to as "oil-seed" crops and include, oilseed rape, canola, soya and sunflower. Methods for the genetic transformation of many oil crops are known; for example, transformation by *Agrobacterium tumefaciens* methods are suitable for most. Such methods are well-described in the literature and well-known and extensively practised in the art.

The biosynthesis of polyhydroxybutyrate from the substrate, acetyl-CoA involves three enzyme-catalysed steps, illustrated in FIG. 1 herewith.

The three enzymes involved are β-ketothiolase, NADP linked acetoacetyl-CoA reductase, and polyhydroxybutyrate synthase, the genes for which have been cloned from *Alcaligenes eutrophus* (Schubert et al, 1988, J Bacteriol, 170). When cloned into *Escherichia coli* the three genes are known to facilitate production of polyhydroxyalkanoate up to 30% of the cell weight.

Genes specifying the production of alkanoates higher than the butyrate are known to exist in bacteria. Isolation of the appropriate genes allows expression of these higher polyhydroxyalkanoates. For example, genes specifying production of the polyhydroxy-octanoate and the decanoate exist in the bacterial species *Pseudomonas oleovorans* and *Pseudomonas eruginosa*. However genes for analogous polymers are widespread in bacterial species.

All the microorganisms required for performance of this invention are publicly available from public culture collections.

An important preferred feature of this invention is the use of an oilseed plant for expression of the polyhydroxyalkanoate. The reason behind our selection of oil-producing crops is that such plants naturally produce large amounts of acetyl-CoA substrate (under aerobic conditions) in the developing seed, which is normally used in fatty acid synthesis. Diversion of this substrate into polyhydroxyalkanoate production will reduce the amount of oil stored by the seed but will have minimal influence on other aspects of the call's metabolism. It is therefore possible to produce commercially viable quantities of polyhydroxyalkanoate such as polyhydroxybutyrate in an oilseed.

It has been previously suggested that *Alcaligenes eutrophus* genes could be expressed in a starch crop but this has certain problems. In order to optimise polyhydroxyalkanoate production in such a crop, it would probably be necessary to down-regulate starch synthesis. However, even if this down-regulation were to be effected it would not guarantee an increased rate of acetyl-CoA production. Moreover, even if this increased production were actually achieved, it is possible that the acetyl-CoA would be rapidly utilised by respiration in the starch crop.

For expression in higher plants the bacterial (for example *Alcaligenes eutrophus*) genes require suitable promoter and terminator sequences. Various promoters/terminators are available for use. For constitutive expression the cauliflower mosaic virus CaMV35S promoter and nos terminator may be used. It is however preferred to target synthesis of polyhydroxyalkanoate only to the developing oil storage organ of the oilseed such as the embryo of oilseed rape. The promoter of the rape seed storage protein, napin, could be used to obtain embryo specific expression of polyhydroxyalkanoate genes. Expression of the polyhydroxyalkanoate genes during the precise period when lipid is being made will ensure effective competition by the polyhydroxyalkanoate enzymes for available acetyl-CoA. The promoters of fatty acid synthesis genes whose expressions are switched on at this time are thus most appropriate candidates to be used as polyhydroxyalkanoate gene promoters. Examples of such promoters are those of seed specific isoforms of rape acyl carrier protein (ACP) or β-ketoacyl ACP reductase.

In inserting the polyhydroxyalkanoate genes into eukaryotic cells, consideration has to be given to the most appropriate subcellular compartment in which to locate the enzymes. Two factors are important: the site of production of the acetyl-CoA substrate, and the available space for storage of the polyhydroxyalkanoate polymer.

The acetyl-CoA required for fatty acid synthesis in, for example, developing rapeseed embryo is produced by two routes. The first, direct, route involves the activity of a pyruvate dehydrogenase enzyme located in the plastid. The second route involves the initial production of acetyl-CoA by mitochondrial pyruvate dehydrogenase, lysis to free acetate, and diffusion of the acetate into the plastid where it is re-esterified to CoA by acetyl-CoA synthase. Rapeseed also produces acetyl-CoA in the cytosol, though at a lower rate than in the plastid, via the activity of a cytosolic citrate lyase enzyme.

Considering substrate supply, the bacterial (for example, Alcaligenes) β-ketothiolase enzyme may function in the mitochondrion, using acetyl-CoA produced in excess of the requirements of respiration, or in the cytosol. The regulatory sequences of the invention may thus direct expression of the β-ketothiolase gene to the mitochondrion or to the cytosol. It is however preferred to target this enzyme to the plastids, where highest rates of acetyl-CoA generation occur.

The mitochondrion lacks sufficient space for storage of the polyhydroxyalkanoate polymer. Significant storage space exists in the plastids, at least in rape embryo. Highest storage space exists in the cytosol, the compartment normally occupied by the oil bodies.

It is not known whether the acetoacetyl-CoA or hydroxybutyryl-CoA pathway intermediates can be transported from plastid to cytosol. Certainly they would not be able to traverse the plastid envelope membrane as CoA esters. Export would require that the acetoacetate or hydroxybutyrate groups are recognised by the transport systems involved in export of fatty acids from plastids. These have been suggested to involve: lysis of the CoA ester, export of the free acid, and resynthesis of the CoA ester in the cytosol; or transfer of the acyl groups to carnitine, and export of acyl carnitine. If acetoacetyl groups may be exported from the plastid by one of these mechanisms then it would be possible to target β-ketothiolase to the plastid, to utilise acetyl-CoA destined for lipid synthesis, and target acetoacetyl-CoA reductase and polyhydroxybutyrate synthase to the cytosol to achieve polymer synthesis in this more spacious compartment. If neither acetoacetate nor hydroxybutyrate groups may be exported from the plastid, polyhydroxyalkanoate synthesis will require that all three pathway enzymes are targeted to this organelle so that they are expressed in the same cell compartment.

To target the three bacterial (such as *Alcaligenes eutrophus*) enzymes for polyhydroxyalkanoate synthesis to the plant plastid requires the use of specific targeting regulatory elements called transit peptides. Possible sources of plastid stroma targeting sequences are the genes for:
(a) ribulose bisphosphate carboxylase/oxygenase small subunit (RUBISCO ssu);
(b) acyl carrier protein (ACP);
(c) β-ketoacyl ACP reductase;
(d) enolpyruvylshikimate-3-phosphate synthase (EPSPS);
(e) fructose 1,6-bisphosphatase.

Of these the RUBISCO small subunit transit peptide has been shown to direct polypeptides to plastids in both photosynthetic and non-photosynthetic tissues. ACP and β-ketoacyl ACP reductase transit peptides would also operate effectively in plants such as rape embryo. The advantage of using the same plastid transit peptide for all three polyhydroxyalkanoate genes is to ensure that any variability in the uptake of the genes is not due to the transit peptide which is used.

Although some proteins appear to be efficiently targeted to the plastid stroma by the transit peptide alone, other proteins also require the presence of up to twenty amino acids of the amino terminus of the mature protein. The requirement for the presence of mature sequences appears to depend on the size and charge of the protein to be transported.

To obtain synthesis of polyhydroxyalkanoate polymer in plant tissues it is necessary to obtain plants expressing all three genes for the enzymes β-ketothiolase, acetoacetyl-CoA reductase and polyhydroxybutyrate synthase. This may be achieved by using one of the following strategies:
i) Plants may be individually transformed with the three polyhydroxyalkanoate pathway genes. Plants containing individual genes are grown up in the glass-house and cross-pollinated to obtain hybrid plants containing two pathway genes. This procedure is then repeated to produce hybrid plants containing all three genes.
ii) Plants may be sequentially transformed with plasmids containing the individual pathway genes.
iii) Two or three pathway genes may be cotransformed into the same plant by simultaneous infection with Agrobacteria containing the individual genes.
iv) Plants may be transformed with plasmids containing two or three pathway genes.

A combination of these techniques may be used to obtain expression of all three genes in a single plant. Successive round of cross-pollination are carried out until the progeny are homozygous for all three genes. For methods (ii) and (iii) above, it is advantageous to insert each gene into vectors containing different selectable marker genes to facilitate selection of plants containing two or three polyhydroxyalkanoate pathway genes. Examples of selectable markers are genes conferring resistances to kanamycin, hygromycin, sulphonamides and bialaphos or phosphinothricin.

The invention will now be described by way of example only with reference to the accompanying drawings, in which:

BRIEF DESCRIPTION OF THE DRAWINGS

FIG. 2 is a physical map of the 5.2 kb SmaI-EcoRI fragment of *Alcaligenes eutrophus* DNA;

FIG. 3 is a map of the plant expression vector pJR1i;

FIG. 6 is a graph of NADP acetoacetyl CoA reductase enzyme activities in tobacco leaves.

DETAILED DESCRIPTION OF THE INVENTION

Example

Figure 1:
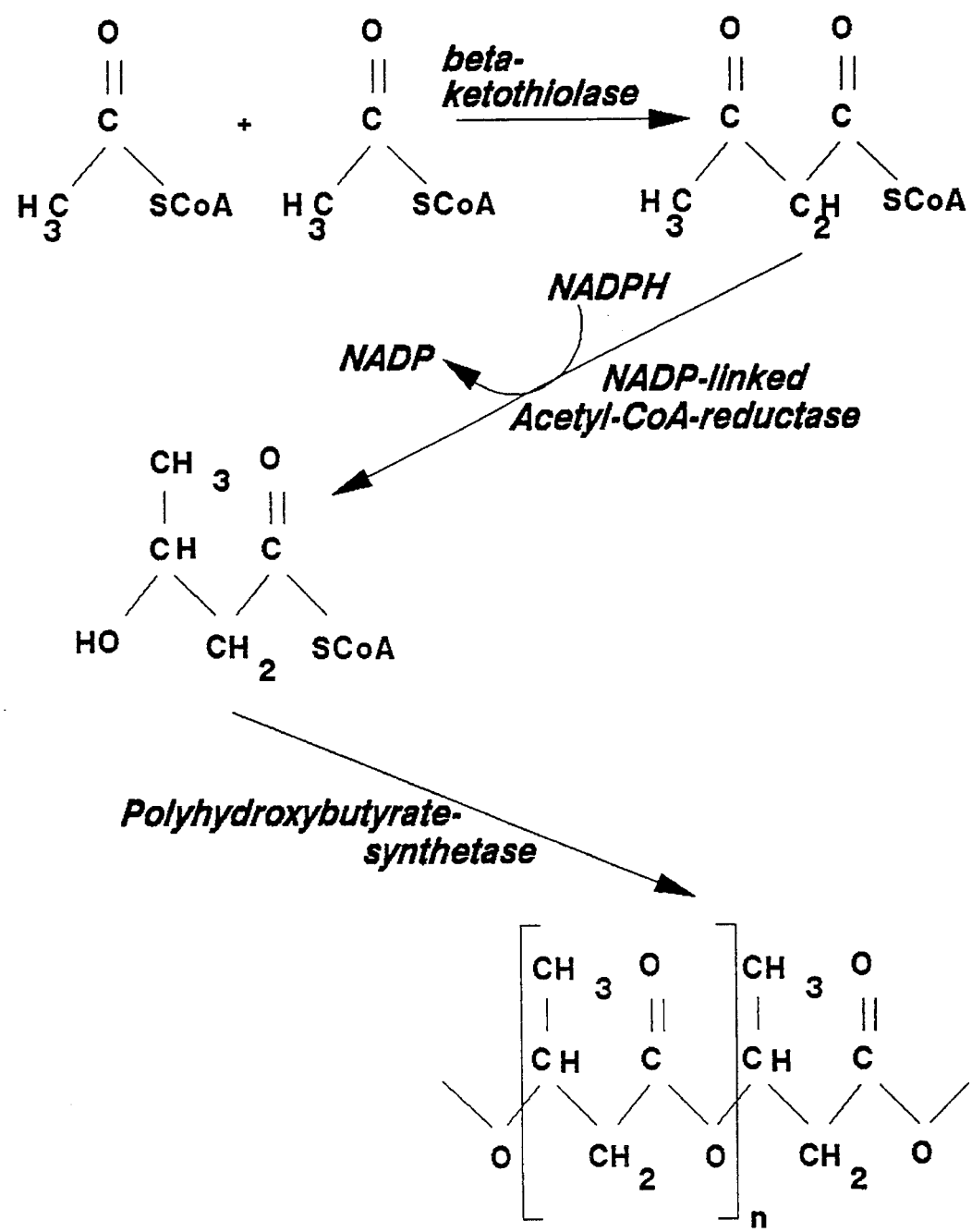
FIG. 1 shows the pathway for polyhydroxybutyrate production in *Alcaligenes eutrophus*.

A 5.2 kb SmaI-EcoRI fragment which codes for all three polyhydroxyalkanoate (PHA) biosynthetic genes had previously been isolated from *Alcaligenes eutrophus* (Schubert et al, 1988, J Bacteriol, 170). This fragment cloned into the vector pUC9 (New England Biolabs) together with a 2.3 kb PstI sub fragment cloned into Bluescript KS- (Stratagene) were provided by Dr Steinbuchel of the University of Gottingen, Germany. A restriction map of the fragment is shown in FIG. 2. The positions of the restriction sites and the positions of the genes for β-ketothiolase, acetoacetyl CoA reductase, and polyhydroxybutyrate (PHB) synthase are shown.

The expression vector chosen to gain constitutive expression of PHA biosynthetic genes in tobacco and oilseed rape plants was pJR1i. This vector contains the cauliflower mosaic virus CaMV35S promoter and the nos terminator, separated by a multiple cloning site to allow the insertion of the PHA genes. The vector also contains the kanamycin resistance nptII gene as a selectable marker. FIG. 3 is a map of the plant expression vector pJR1i. Vector pJR1Ri was also utilised; this vector contains the expression cassette in the opposite orientation.

All routine molecular biological techniques were those of Sambrook et al (1989, A laboratory manual, Second edition). Oligonucleotides were all synthesised on an Applied Biosystems 380B DNA Synthesiser. PCR machines used were Techne PHC-1 Programmable Dri-Blocks. Taq polymerase was obtained from Perkin-Elmer/Cetus. Restriction enzymes and other modifying enzymes were obtained from New England Biolabs, Gibco/BRL, Northumbria Biologicals Limited and Pharmacia. Sequencing kits were obtained from Cambridge Biosciences (Sequenase) and Promega (Taqtrack). All radio-isotopes were supplied by Amersham International.

1. Construction of vectors to gain constitutive cytosolic expression of PHA pathway genes

1.1. β-ketothiolase

The β-ketothiolase gene was isolated as a 1.3 kb PstI-PleI fragment from the 2.3 kb PstI fragment of pKS-::2.3 P7. This fragment was blunt-ended with Klenow and was inserted into the dephosphorylated SmaI site of pJR1i. The resulting plasmid was denoted pJR1iT. Recombinant plasmids were identified by colony hybridisation using the 1.3 kb insert fragment as a probe. Restriction mapping of recombinants revealed those containing a single β-ketothiolase insert in the sense orientation. The orientation of the insert was confirmed by sequencing using a primer that hybridised to the 3' end of the CaMV35S promoter.

1.2. Acetyoacetyl-CoA reductase

The acetoacetyl-CoA reductase gene was isolated as a 0.9 kb AvaII-XmnII fragment from pKS::2.3P7. This fragment was inserted into pJRIi as described for pJRIiT. However, the orientation of the insert fragment in recombinant plasmids could not be confirmed by restriction mapping due to the unavailability of suitable restriction enzyme sites. Therefore four recombinants were sequenced using the CaMV35S 3' primer and, of these, one was found to contain a sense insert. This plasmid was denoted pJR1iR.

1.3. PHB synthase

The PHB synthase gene was isolated from pKS::2.3p7 as a BstBi-StuI fragment. This fragment was blunt-ended and inserted into pJRIi as described for pJRIiT and pJRIiR. The identity of recombinant (pJRIiS) plasmids containing a single insert in the sense orientation ws confirmed by restriction mapping and by sequencing with the CaMV35S 3' primer.

2. Construction of vectors for constitutive plastid targeted expression of PHA pathway enzymes.

Transport into plastids of the component polypeptides for each of the PHB pathway enzymes can be achieved by addition of a transit peptide sequence to the 5' end of the gene sequence.

The first gene to be tailored was ketothiolase. A technique involving polymerase chain reaction (PCR) was employed in order to join the pea RUBISCO small subunit transit peptide sequence in frame with the ketothiolase gene.

Linking the transit peptide to the ketothiolase gene involved three experiments. The first experiment added a small portion of the 5' end of the ketothiolase gene onto the 3' end of the transit peptide sequence. The second experiment added a small portion of the 3' end of the transit peptide onto the 5' end of ketothiolase gene. The third experiment utilised the overhangs produced in the preceding experiments to extend across the junction and produce full length transit peptide linked in frame with the ketothiolase gene. Four PCR primers were designed:

1. 5' end of the transit peptide allowing extension toward its 3' end: (see SEQ ID NO: 1)

AAA TGG CTT CTA TGA TAT CCT CTT CAG CT
   TP1

2. 3' end of transit peptide linked to 5' end of ketothiolase gene allowing extension toward 5' end of transit peptide: (see SEQ ID NO: 2)

ACG ATG ACA ACG T CA GTC ATG CAC TTT ACT CTT CCA CCA TTG CTT GT
   TPKB 3. 3' end of transit peptide linked to 5' end of ketothiolase gene allowing extension toward the 3' end of the ketothiolase gene: (see SEQ ID NO: 3)

ATT ACA AGC AAT GGT GGA AGA GTA AAG TGC
ATG ACT GAC GTT GTC ATC GT

TPKT 4. 3' end of ketothiolase gene: (see SEQ ID NO: 4)

ACC CCT TCC TTA TTT GCG CTC GAC T

K1

For the first experiment template DNA was pSM64 (transit peptide sequence) and the primers were TP1 and TPKB with an annealing temperature of 65° C. The derived PCR products were run out on an agarose gel and the band corresponding to 199 bp cut out and electroeluted from the gel.

In the second experiment template DNA was pKS::2.3 P7, the primers involved were TPKT and K1 and the annealing temperature 68° C. The products of the PCR reaction were again run out on a gel and the required 1.207 kb band isolated and electroeluted from the gel slice.

The third experiment utilised the DNA isolated from the previous experiment as template and the primers TP1 and K1. The annealing temperature was 65° C. and although this PCR experiment was very inefficient some full length product (1.352 kb) was formed.

Figure 4:
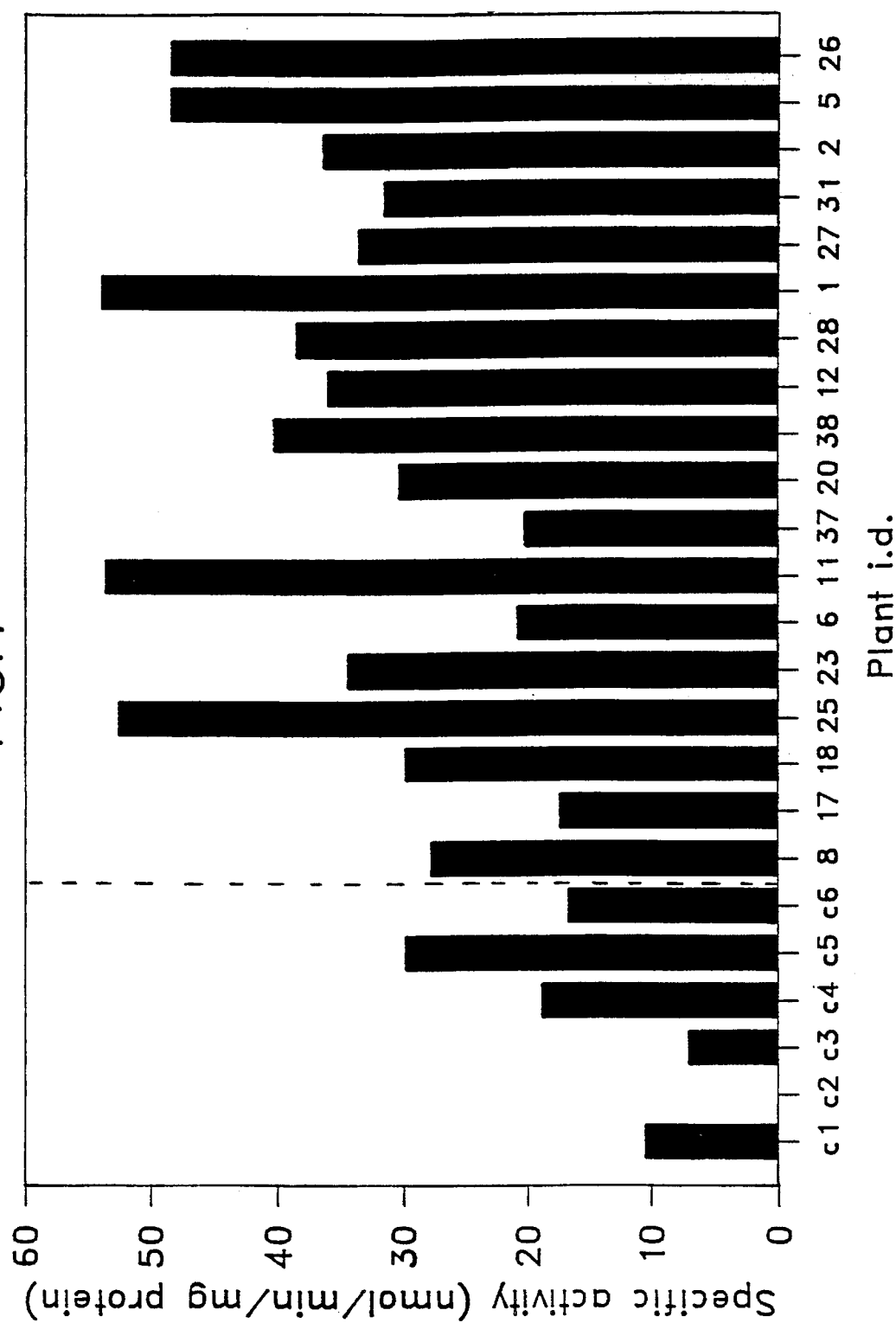
FIG. 4 shows the Southern blot analysis of the three PCR products produced during the making of the ssu transit peptide-ketothiolase construct.

A small portion of each of the three PCR products was run out on an agarose gel. Southern blot analysis using three of the oligos as probes (TP1, K1 and TPKT) was carried out. Results are given in FIG. 4 and show that the product of the third reaction contained the 5' end of the transit peptide, the overlap of 3' transit peptide and 5' ketothiolase gene, and the 3' end of the ketothiolase gene.

It was necessary to check the sequence of this product as it is known that PCR can incorporate base mismatches. The PCR product was blunt-ended and cloned into SmaI cut and phosphatased pUC18. Six clones were identified which contained the PCR product. The clones were sequenced using the universal and reverse primers (Sequenase kit and Taqtrack kit). Clones with completely correct sequence through the transit peptide and the 5' end of the ketothiolase gene up to a TthIII1 restriction site within the gene were identified. From one of these clones a TthIII1-KpnI fragment was excised. The KpnI site was cut back to give a blunt end, and a TthIII1-SmaI fragment of *Alcaligenes eutrophus* DNA from pKS-::2.3P7 corresponding to the major portion of the ketothiolase gene was inserted. Positive clones were sequenced across the joins. The transit peptide-ketothiolase fragment was excised and inserted into pJR1Ri.

For the transit peptide-reductase construct PCR was also utilised. This required only one PCR experiment as a Dde I site (unique in the transit peptide and reductase sequences) was present close to the 5' end of the gene. The PCR experiment required two primers:

1. Sequence homologous to the 5' end of the transit peptide which would allow extension toward the 3' end. A Cla I site was incorporated into the sequence 5' to the transit peptide sequence.

ACC ATC GAT GGA TGG CTT CTA TGA TAT CCT CTT
CAG CT (see SEQ ID NO: 5)

CLATP

2. Sequence homologous to just past the Dde I site in the reductase gene, linked in frame with 3' transit peptide sequence to allow extension toward the 5' transit peptide.

ATG CGC TGA GTC ATG CAC TTT ACT CTT CCA CCA
TTG CTT GT A AT (see SEQ ID NO: 6)

TPDDER

After PCR with these two primers and transit peptide DNA as template the 195 bp product was identified on agarose gels and isolated by electroelution. DdeI XmnI reductase gene was isolated and ligated to DdeI cut PCR product. After agarose gel electrophoresis the 1.063 kb band was isolated, cut with ClaI and ligated into ClaI EcoRV Bluescript SK(−). Positives are being characterised.

3. Transformation of plants with the PHB genes 3.1. Agrobacterium transformations Cesium-pure pJRIiT, pJRIiR, pJRIiS and pJRIi were individually transformed into *Agrobacterium tumefaciens* strain LBA4404 by direct uptake as follows. LB (10 mls) was inoculated with *A tumefaciens* strain LBA4404. The culture was shake-incubated at 28° C. for approximately 16 hours until the optical density (OD) at 660 nm was 0.5. The cells were recovered by centrifugation (3000 rpm Sorvall RT6000B, 6 mins, 4° C.). They were resuspended in 250 µl of ice-cold 20 mM $CaCl_2$. The cell suspension was then dispensed into pre-chilled Eppendorf tubes in 0.1 ml aliquots. Approximately 1 µg of caesium-pure plasmid DNA was added to each tube. The cells were then heat-shocked by freezing in liquid nitrogen followed by incubation at 37° C. for 5 minutes. LB medium (1 ml) was added and the cells were allowed to recover by incubation (shaken) at 28° C. for 3–4 hours. The cell pellets were obtained by centrifugation (11,500 g, 30 seconds, 20° C.) and resuspended in 0.1 ml LB. Recombinant cells were selected on LB (agar-solidified) containing kanamycin (50 µg/ml), streptomycin (500 µg/ml) and rifampicin (100 µg/ml) following incubation at 28° C. Mini-prep DNA of the resultant Agrobacterium strains was then isolated and analysed by restriction enzyme digestion to ensure that no re-arrangements had occurred.

3.2. Plant Transformations

Tobacco leaf pieces and oilseed rape petioles were inoculated individually with strains LBA4404/JRIi, LBA4404/pJRIiT, LBA4404/pJRIiR and LBA4404/pJRIiS. Plants were cultured in a growth room with a temperature of 25° C. and a photoperiod of 16 hours.

*Brassica napus* cv. Westar seedlings were sterilised in 10% sodium hypochlorite and washed in sterile water before germination on MS medium (Imperial)(containing 3% sucrose and 0.7% phytagar (Gibco). The cotyledons were excised from 5 day old seedlings and the petioles of which were placed in MS medium as above but supplemented with 4.5 µg/ml benzylaminopurine (BAP). The cotyledons were cultured in this medium for 24 hours after which their petioles were dipped in an Agrobacterium solution. The Agrobacterium culture had been grown overnight in LB medium containing kanamycin (50 µg/ml) following which the Agrobacterium cells had been pelleted and washed in liquid MS medium and diluted to $OD_{660}$ 0.1. The inoculated petioles were returned to the MS medium containing 4.5 µg/ml BAP and incubated in the culture room for 2 days. The cotyledons were then transferred to MS medium supplemented with BAP (4.5 µg/ml), carbenicillin (Duchefa) (500 µg/ml) and kanamycin (15 µg/ml). The cotyledons were subcultured on this medium every 2 weeks until the production of green callus and eventually shoots. Shoots were excised and cultured on MS containing carbenicillin (500 μg/ml) and kanamycin (15 μg/ml) until they were transferred to the glasshouse.

*Nicotiana tabacum* cv SRI seeds were sterilised as described above and germinated on MS medium (containing 3% sucrose and 0.8% bactoagar). The shoot tips from these seedlings were then micropropagated on this media to provide plants for transformation studies. Leaf pieces from these plants were dipped in an Agrobacterium solution (prepared as described above) and were then cultured on MS medium containing 3% sucrose, 0.8% bactoagar, 1 μg/ml BAP and 0.1 μg/ml NAA, for 2 days. The leaf pieces were then cultured on the same media supplemented with carbenicillin (500 μg/ml) and kanamycin (100 μg/ml) for 5 weeks. Regenerated shoots were excised and cultured on MS containing 3% sucrose, 0.8% bactoagar, 200 μg/ml carbenicillin and 100 μg/ml kanamycin for 2 passages of 5 weeks before transfer to the glasshouse.

Kanamycin-resistant tobacco and rape plants were obtained for those transformed individually with JR1i, JR1iT, JR1iR and JR1iS.

3.3. Cotransformations

Rape cotyledons and tobacco leaf pieces were also inoculated with mixtures of Agrobacterium strains. These inoculations were performed as described previously except that 1:1 mixtures of diluted Agrobacterium cultures, of the same optical density, were prepared immediately prior to inoculation.

4. Biochemical assessment of plants

Expression of *Alcaligenes eutrophus* PHA pathway enzymes in plant tissues was detected by enzyme activity assays. The presence of the enzyme polypeptides was also detected by Western blot analysis.

For the latter analyses rabbit polyclonal antibodies were raised to the purified β-ketothiolase and NADP acetoacetyl CoA reductase enzymes from *Alcaligenes eutrophus*. Bacteria were pelleted, washed, and crude extracts prepared as described by Haywood and Large (1981, Biochem J, 199, 187–201). β-ketothiolase A was purified by chromatography on hydroxylapatite, followed by anion exchange chromatography on FPLC mono Q, followed by gel filtration on Superdex S-200 (Pharmacia), using modifications of methods described by Haywood et al (1988, FEMS Microbiology Letters, 52, 91–96). NADP acetoacetyl-CoA reductase was purified using the same techniques, with an additional affinity chromatography step on 2',5' ADP sepharose (Pharmacia). Purified proteins were subjected to sodium dodecyl sulphate polyacrylamide gel electrophoresis (SDS PAGE) according to the method of Laemmli (1970, Nature, 222, 680–685). The final β-ketothiolase preparation showed a single coomassie blue stained band at 41 kd. The final reductase preparation showed a major band at 26 kd. 3 mg of purified ketothiolase and 2 mg of purified reductase were subjected to preparative SDS PAGE. The bands corresponding to the two enzymes were electroeluted from the gels and injected into rabbits to raise polyclonal antibodies. Sera from primary and secondary bleeds following injection were shown to contain antibodies specific for their target enzymes via Western blot analyses of crude Alcaligenes extracts.

Crude extracts of tobacco leaves were prepared by grinding leaf tissue in 50 mM potassium phosphate buffer pH 7.0 containing 1 mM dithiothreitol. After centrifugation at 30,000 g, enzyme assays for ketothiolase and acetoacetyl CoA reductase were conducted on aliquots of the supernatants by the methods described by Haywood et al (1988, FEMS Microbiology Letters, 52, 91–96; 52, 259–264). PHB synthase assays were conducted on aliquots of the 30,000 g supernatants and aliquots of the pellets, resuspended in extraction buffer, by the method of Haywood et al (1989, FEMS Microbiology Letters, 57, 1–6).

For Western blot analysis, aliquots of the 30,000 g supernatants were subjected to SDS PAGE and electrophoretically transferred to nitrocellulose filters. Filters were then rinsed in TBS (50 mM Tris-HCl pH 7.9, 150 mM NaCl) and incubated in TBS plus 5% bovine serum albumin. Proteins reacting with anti-ketothiolase or anti-reductase serum were detected by incubating the filters in 100 ml TBS containing 2 ml of the relevant serum for 1–2 h. Bound first antibody was subsequently detected using goat anti-rabbit IgG alkaline phosphatase conjugate and nitroblue tetrazolium alkaline phosphatase colour development reagent (BioRad Laboratories).

Initial biochemical analyses were carried out on subcultured tobacco plants growing in tissue culture. Eighteen kanamycin resistant plants transformed with JR1i ketothiolase were subjected to enzyme analysis and results compared with untransformed control plants. Leaves of the same size were extracted.

Figure 5:
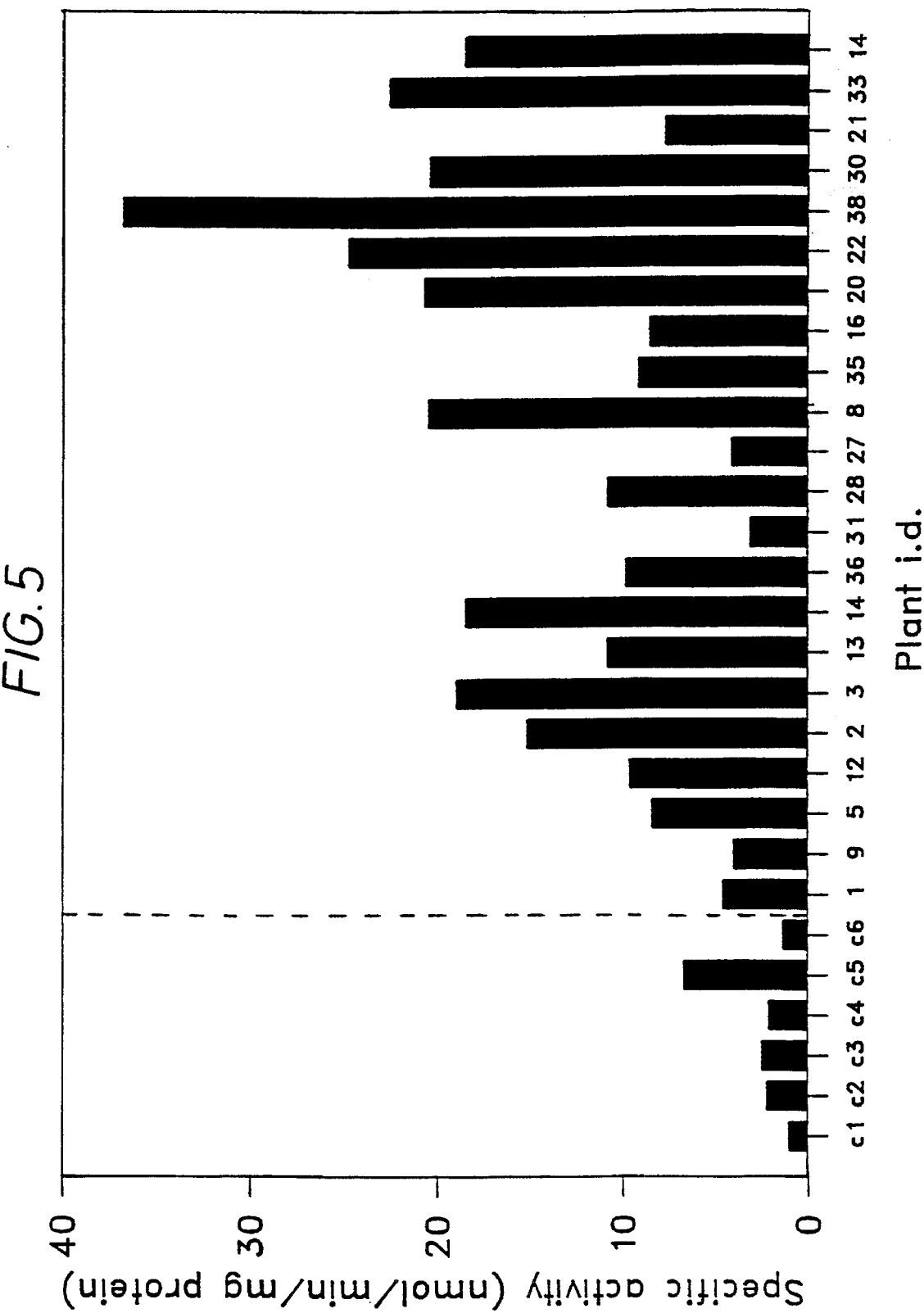
FIG. 5 is a graph of β-ketothiolase enzyme activities in tobacco leaves.

FIG. 5 shows the β-ketothiolase enzyme activities in the tobacco leaves. The identification numbers of individual plants are shown on the x axis. Plants to the left of the dotted line are untransformed control plants. Plants to the right of the line are transformed with JR1i ketothiolase.

A low level of ketothiolase activity was detected in untransformed control plants. Nearly all of the JR1i ketothiolase transformed plants had ketothiolase activity higher than control. The highest activity was 34 nmol/min/mg protein, 2.8 times higher than the highest control plant. In Western blots the anti-ketothiolase antibody detected a polypeptide at 41 kd in untransformed control tobacco plants—possibly corresponding to the endogenous ketothiolase enzyme activity. While a 41 kd polypeptide was also detected in extracts of JR1i ketothiolase transformed plants, the Western blots could not quantitatively distinguish transformed from untransformed plants.

FIG. 6 shows the NADP acetoacetyl CoA reductase enzyme activities in leaves of the tissue culture grown tobacco plants. The identification numbers of individual plants are shown on the x axis. Plants to the left of the dotted line are untransformed control plants. Plants to the right of the line are transformed with pJR1i reductase.

A low level of acetoacetyl CoA reductase activity was detected in untransformed control plants. Nearly all the 21 JR1i reductase transformed plants had reductase activity higher than control. The highest activity was 30 nmol/min/mg protein, 4 fold higher than the highest control plant. In Western blots the anti-reductase antibody did not detect any polypeptide with a m.w. of 26 kd in extracts of untransformed control plants. A 26 kd polypeptide was however detected in extracts of the JR1i reductase transformed plants. Expression of the bacterial reductase gene in tobacco leaves was therefore demonstrated.

We claim:

1. A *Brassica napus* plant adapted for the production of polyhydroxyalkanoate comprising a recombinant genome of a *Brassica napus* plant, which genome contains genes encoding β-ketothiolase, acetoacetyl-Coenzyme A reductase and polyhydroxyalkanoate synthase for catalysing the production of polyhydroxyalkanoate together with gene regulatory sequences, including seed specific gene regulatory sequences directing expression of the said genes to the seed of said *Brassica napus* plant.

2. A plant according to claim 1 wherein the genes encoding the enzymes necessary for the catalysis of polyhydroxyalkanoate production are isolated from a micro-organism.

3. A plant according to claim 2 wherein the micro-organism is *Alcaligenes eutrophus*.

4. A plant as claimed in claim 1, in which expression is directed to the developing seed.

5. A plant as claimed in claim 1, in which expression is directed to the embryo.

6. A plant as claimed in claim 1, in which the said gene regulatory sequences direct expression of the polyhydroxyalkanoate genes to the cytosol or to the mitochondrion or to the plastid.

\* \* \* \* \*